United States Patent
Moore et al.

(10) Patent No.: US 10,500,061 B2
(45) Date of Patent: Dec. 10, 2019

(54) ADJUSTABLE SPINAL IMPLANT

(71) Applicant: K2M, Inc., Leesburg, VA (US)

(72) Inventors: Jennifer Moore, Leesburg, VA (US); Stephen Truesdell, Reston, VA (US)

(73) Assignee: K2M, Inc., Leesburg, VA (US)

( * ) Notice: Subject to any disclaimer, the term of this patent is extended or adjusted under 35 U.S.C. 154(b) by 5 days.

(21) Appl. No.: 15/752,369

(22) PCT Filed: Aug. 15, 2016

(86) PCT No.: PCT/US2016/046991
§ 371 (c)(1),
(2) Date: Feb. 13, 2018

(87) PCT Pub. No.: WO2017/027873
PCT Pub. Date: Feb. 16, 2017

(65) Prior Publication Data
US 2019/0000644 A1    Jan. 3, 2019

Related U.S. Application Data

(60) Provisional application No. 62/204,542, filed on Aug. 13, 2015.

(51) Int. Cl.
*A61F 2/44*   (2006.01)
*A61F 2/46*   (2006.01)
*A61F 2/30*   (2006.01)

(52) U.S. Cl.
CPC .......... *A61F 2/4465* (2013.01); *A61F 2/4455* (2013.01); *A61F 2/4611* (2013.01);
(Continued)

(58) Field of Classification Search
CPC .......... A61F 2/4455–447; A61F 2/4425; A61F 2002/30537–30538
See application file for complete search history.

(56) References Cited

U.S. PATENT DOCUMENTS 9,801,734 B1 * 10/2017 Stein ................... A61F 2/447
9,987,146 B1 *  6/2018 Lentner .............. A61F 2/4637
(Continued)

OTHER PUBLICATIONS

International Search Report dated Oct. 28, 2016 in PCT/US2016/046991.
(Continued)

*Primary Examiner* — Eduardo C Robert
*Assistant Examiner* — Michelle C Eckman
(74) *Attorney, Agent, or Firm* — Lerner, David, Littenberg, Krumholz & Mentlik, LLP

(57) ABSTRACT

An adjustable spinal implant includes a fixed segment that slidably supports a locking segment and pivotally supports an upper segment and a lower segment relative to one another. The locking segment translates within a channel defined by the fixed segment between locked and unlocked positions. In the locked position, the upper and lower segments are fixed relative to one another and to the fixed segment. In the unlocked position, the upper and lower segments are pivotal relative to one another and to the fixed segment. The adjustable spinal implant includes a locking mechanism including a locking screw to translate the locking segment between locked and unlocked positions.

20 Claims, 5 Drawing Sheets

(52) U.S. Cl.
CPC ............... *A61F 2002/3052* (2013.01); *A61F 2002/30405* (2013.01); *A61F 2002/30471* (2013.01); *A61F 2002/30507* (2013.01); *A61F 2002/30538* (2013.01); *A61F 2002/30556* (2013.01); *A61F 2002/30579* (2013.01); *A61F 2002/30772* (2013.01); *A61F 2002/30822* (2013.01); *A61F 2002/30904* (2013.01)

(56) References Cited

U.S. PATENT DOCUMENTS

| | | | |
|---|---|---|---|
| 10,022,239 B1* | 7/2018 | Lentner | A61F 2/4425 |
| 2002/0128713 A1* | 9/2002 | Ferree | A61F 2/2846 623/17.11 |
| 2003/0236520 A1* | 12/2003 | Lim | A61B 17/025 606/99 |
| 2004/0044411 A1* | 3/2004 | Suddaby | A61F 2/28 623/17.15 |
| 2005/0113916 A1* | 5/2005 | Branch, Jr. | A61F 2/447 623/17.11 |
| 2006/0030943 A1* | 2/2006 | Peterman | A61F 2/4455 623/17.11 |
| 2009/0265007 A1 | 10/2009 | Colleran | |
| 2010/0191336 A1* | 7/2010 | Greenhalgh | A61F 2/4455 623/17.16 |
| 2010/0324687 A1 | 12/2010 | Melkent et al. | |
| 2012/0303124 A1* | 11/2012 | McLuen | A61F 2/4455 623/17.16 |
| 2013/0131808 A1* | 5/2013 | Suh | A61F 2/30721 623/17.16 |
| 2013/0158664 A1* | 6/2013 | Palmatier | A61F 2/447 623/17.16 |
| 2013/0197642 A1* | 8/2013 | Ernst | A61F 2/442 623/17.16 |
| 2013/0274883 A1* | 10/2013 | McLuen | A61F 2/447 623/17.16 |
| 2014/0094922 A1* | 4/2014 | Abdou | A61F 2/44 623/17.16 |
| 2014/0114420 A1* | 4/2014 | Robinson | A61F 2/447 623/17.16 |
| 2014/0148904 A1* | 5/2014 | Robinson | A61F 2/447 623/17.16 |
| 2014/0194991 A1* | 7/2014 | Jimenez | A61F 2/447 623/17.15 |
| 2014/0257486 A1* | 9/2014 | Alheidt | A61F 2/447 623/17.15 |
| 2014/0277508 A1* | 9/2014 | Baynham | A61F 2/447 623/17.16 |
| 2014/0296983 A1* | 10/2014 | Fauth | A61F 2/447 623/17.16 |
| 2014/0316522 A1* | 10/2014 | Weiman | A61F 2/4455 623/17.16 |
| 2014/0343677 A1* | 11/2014 | Davis | A61F 2/447 623/17.15 |
| 2014/0343678 A1* | 11/2014 | Suddaby | A61F 2/46 623/17.16 |
| 2015/0018954 A1* | 1/2015 | Loebl | A61F 2/4425 623/17.16 |
| 2015/0057755 A1* | 2/2015 | Suddaby | A61F 2/4425 623/17.16 |
| 2015/0148908 A1* | 5/2015 | Marino | A61F 2/4455 623/17.16 |
| 2015/0257894 A1* | 9/2015 | Levy | A61F 2/442 623/17.15 |
| 2015/0272743 A1* | 10/2015 | Jimenez | A61F 2/447 623/17.16 |
| 2015/0351925 A1* | 12/2015 | Emerick | A61F 2/447 623/17.16 |
| 2015/0374508 A1* | 12/2015 | Sandul | A61F 2/447 623/17.16 |
| 2016/0022438 A1* | 1/2016 | Lamborne | A61F 2/4455 623/17.16 |
| 2016/0030190 A1* | 2/2016 | Robinson | A61F 2/447 623/17.16 |
| 2016/0038305 A1* | 2/2016 | Weiman | A61F 2/4455 623/17.16 |
| 2016/0089247 A1* | 3/2016 | Nichols | A61F 2/30767 623/17.16 |
| 2016/0095716 A1* | 4/2016 | Baynham | A61F 2/44 623/17.16 |
| 2016/0100951 A1* | 4/2016 | Suddaby | A61F 2/442 623/17.16 |
| 2016/0100955 A1* | 4/2016 | Stinchfield | A61F 2/4465 623/17.15 |
| 2016/0120660 A1* | 5/2016 | Melkent | A61F 2/4455 623/17.16 |
| 2016/0166396 A1* | 6/2016 | McClintock | A61F 2/30771 623/17.16 |
| 2016/0206440 A1* | 7/2016 | Deridder | A61F 2/4455 |
| 2016/0250034 A1* | 9/2016 | Loebl | A61F 2/44 623/17.16 |
| 2016/0278935 A1* | 9/2016 | Overes | A61F 2/442 |
| 2016/0324654 A1* | 11/2016 | Loebl | A61F 2/4455 |
| 2016/0331542 A1* | 11/2016 | Faulhaber | A61F 2/447 |
| 2016/0354211 A1* | 12/2016 | Packer | A61F 2/447 |
| 2016/0354212 A1* | 12/2016 | Baynham | A61F 2/447 |
| 2017/0042695 A1* | 2/2017 | Foley | A61F 2/4455 |
| 2017/0056197 A1* | 3/2017 | Weiman | A61F 2/447 |
| 2017/0100255 A1* | 4/2017 | Hleihil | A61F 2/447 |
| 2017/0105844 A1* | 4/2017 | Kuyler | A61F 2/447 |
| 2017/0112630 A1* | 4/2017 | Kuyler | A61F 2/447 |
| 2017/0112631 A1* | 4/2017 | Kuyler | A61F 2/4455 |
| 2017/0112632 A1* | 4/2017 | Dmushewsky | A61F 2/44 |
| 2017/0119538 A1* | 5/2017 | Baynham | A61F 2/4455 |
| 2017/0119543 A1* | 5/2017 | Dietzel | A61F 2/447 |
| 2017/0156885 A1* | 6/2017 | Zur | A61F 2/4611 |
| 2017/0172758 A1* | 6/2017 | Field | A61F 2/442 |
| 2017/0181863 A1* | 6/2017 | Bjork | A61F 2/447 |
| 2017/0189200 A1* | 7/2017 | Miller | A61F 2/447 |
| 2017/0216045 A1* | 8/2017 | Dewey | A61F 2/447 |
| 2017/0231778 A1* | 8/2017 | Overes | A61F 2/4455 623/17.16 |
| 2017/0246006 A1* | 8/2017 | Carnes | A61F 2/447 |
| 2017/0296352 A1* | 10/2017 | Richerme | A61F 2/447 |
| 2017/0304071 A1* | 10/2017 | Black | A61F 2/4425 |
| 2017/0312090 A1* | 11/2017 | Sharabani | A61F 2/44 |
| 2017/0319352 A1* | 11/2017 | Dewey | A61F 2/4425 |
| 2017/0333199 A1* | 11/2017 | Sharifi-Mehr | A61F 2/4455 |
| 2017/0333200 A1* | 11/2017 | Arnin | A61F 2/4425 |
| 2017/0367843 A1* | 12/2017 | Eisen | A61F 2/30734 |
| 2017/0367845 A1* | 12/2017 | Eisen | A61F 2/4425 |
| 2018/0014947 A1* | 1/2018 | Baynham | A61F 2/30771 |
| 2018/0036137 A1* | 2/2018 | Levieux | A61F 2/4455 |
| 2018/0071111 A1* | 3/2018 | Sharifi-Mehr | A61F 2/441 |
| 2018/0116811 A1* | 5/2018 | Bernard | A61F 2/30767 |
| 2018/0116812 A1* | 5/2018 | Bernard | A61F 2/4455 |
| 2018/0116815 A1* | 5/2018 | Kuyler | A61F 2/447 |
| 2018/0125671 A1* | 5/2018 | Bernard | A61F 2/30771 |
| 2018/0185164 A1* | 7/2018 | Sharabani | A61F 2/4425 |
| 2018/0289499 A1* | 10/2018 | Robinson | A61F 2/447 |
| 2018/0303621 A1* | 10/2018 | Brotman | A61F 2/4455 |
| 2018/0360615 A1* | 12/2018 | Miller | A61F 2/4455 |
| 2018/0360616 A1* | 12/2018 | Luu | A61F 2/4425 |
| 2018/0368983 A1* | 12/2018 | Werner | A61F 2/442 |
| 2019/0000644 A1* | 1/2019 | Moore | A61F 2/4455 |
| 2019/0021868 A1* | 1/2019 | Ludwig | A61F 2/442 |
| 2019/0053912 A1* | 2/2019 | Suddaby | A61F 2/447 |
| 2019/0083279 A1* | 3/2019 | Suddaby | A61F 2/447 |

OTHER PUBLICATIONS

International Preliminary Report on Patentability dated Feb. 13, 2018, issued in PCT/US2016/046991.

* cited by examiner

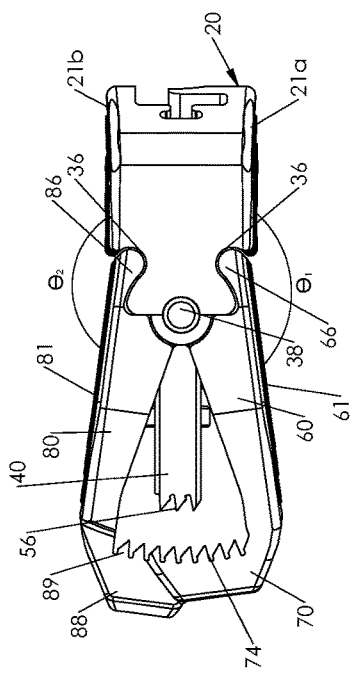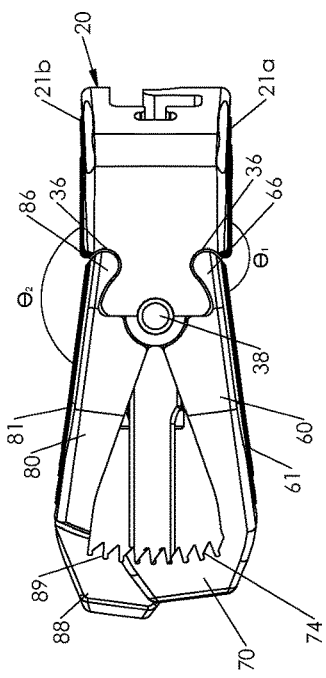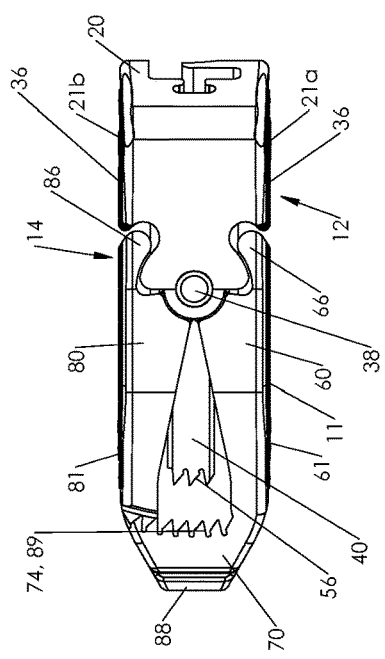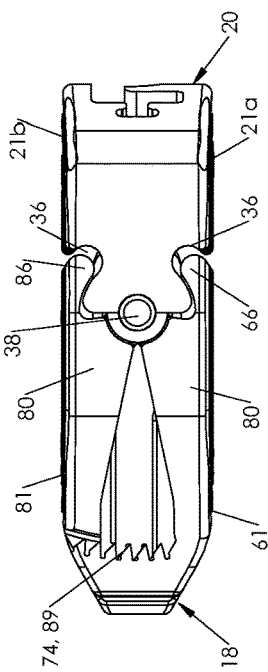

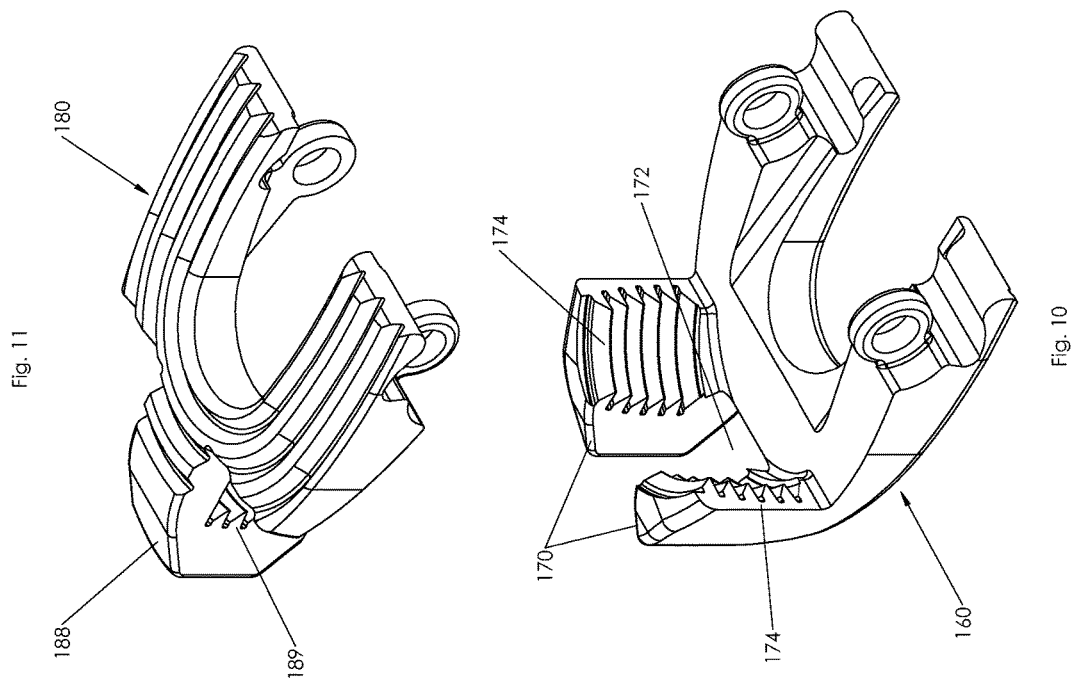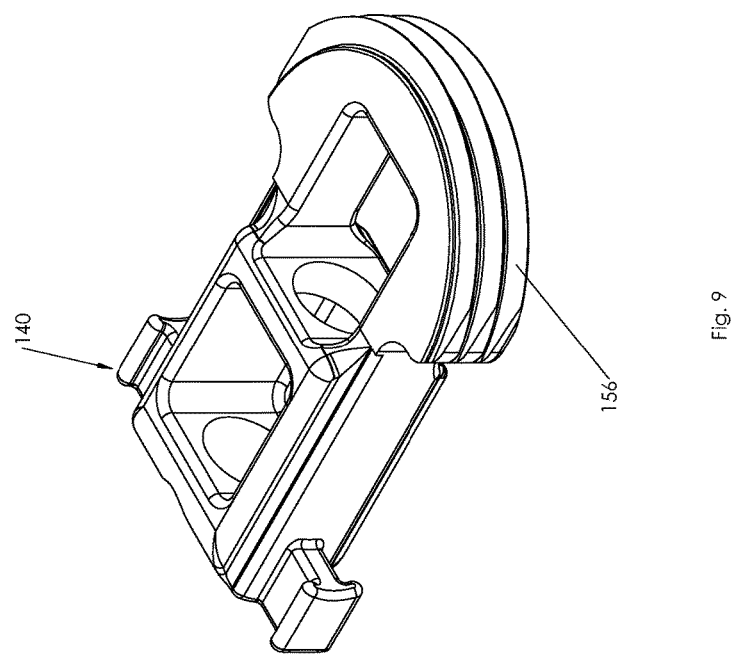

ADJUSTABLE SPINAL IMPLANT

CROSS-REFERENCE TO RELATED APPLICATIONS

This application is a National Stage Entry of PCT/US2016/046991, filed Aug. 15, 2016, which claims the benefit of, and priority to, U.S. Provisional Patent Application Ser. No. 62/204,542, filed Aug. 13, 2015. The entire contents of each of the above applications are hereby incorporated by reference.

BACKGROUND

1. Technical Field

The present disclosure relates to a device for use in orthopedic surgeries and, more specifically, to an adjustable spinal implant and a method for inserting an adjustable spinal implant into an intervertebral space.

2. Discussion of Related Art

Stresses acting upon the human spine (or "vertebral column") may result in a variety of problems or disease states. For example, intervertebral discs have a high propensity to degenerate. Overt or covert trauma occurring in the course of repetitive activities disproportionately affects the more highly mobile areas of the spine. Disruption of a disc's internal architecture leads to bulging, herniation, or protrusion of pieces of the disc and eventual disc space collapse. Any resulting irritation (e.g., mechanical or chemical) of surrounding neural elements (e.g., spinal cord and nerves) may cause pain that is attended by varying degrees of disability. In addition, loss of disc space height relaxes tension on the longitudinal spinal ligaments, thereby contributing to varying degrees of spinal instability such as spinal curvature.

The time-honored method of addressing the issues of neural irritation and instability resulting from severe disc damage have largely focused on removal of the damaged disc and fusing the adjacent vertebral elements together. Removal of the disc relieves the mechanical and chemical irritation of neural elements, while osseous union (i.e., bone knitting) solves the problem of instability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, interbody fusion using bone alone may have an unacceptable rate of bone graft migration, expulsion, or nonunion due to structural failures of the bone or residual degrees of motion that retard or prohibit bony union. Intervertebral prostheses in various forms have therefore been used to provide immediate stability and to protect and preserve an environment that fosters growth of grafted bone such that a structurally significant bony fusion can occur.

Limitations of present-day intervertebral implants can be significant and revolve largely around the marked variation in disc space shape and height which results from either biologic variability or pathologic change. For example, if a disc space is 20 mm in height, a circular implant bridging this gap requires a minimum height of 20 mm just to contact the end plate of the vertebral bone. Generally, end plate disruption must occur to allow a generous bony union, meaning that an additional 2-3 mm must be added on either end, resulting in a final gap or space of 24-26 mm to accommodate the implant. During implantation from an anterior approach (i.e., from the front of the body), excessive retraction (i.e., pulling) is often required on the great blood vessels. On the other hand, during a posterior approach, large implant diameters may require excessive traction on neural elements for adequate placement, even if all posterior bony elements are removed. In some instances, an adequate implant size cannot be inserted posteriorly, particularly if there is a significant degree of ligamentous laxity requiring higher degrees of distraction to obtain stability by tightening the annular ligamentous tension band. Compromising on implant size risks sub-optimal stability or a loose implant, which has a greater chance for migration within or expulsion from the disc space. The alternative of excessively retracting neural elements to facilitate a posterior implant application may result in damage to the neural elements.

Therefore, a need exists for an adjustable implant that can be inserted in a collapsed position in order to prevent over retraction of the anatomy or substandard implant sizing and once the implant is in place be expanded to fill the anatomical space appropriately including a desired amount of lordosis.

SUMMARY

Adjustable spinal implants may serve to stabilize adjacent vertebral elements, thereby facilitating the development of a bony union between them and thus long term spinal stability while being inserted in a collapsed position.

In an aspect of the present disclosure, an adjustable spinal implant includes a fixed segment, a locking segment, a lower segment, an upper segment, and a locking mechanism. The fixed segment defines a channel that is disposed about a longitudinal axis of the spinal implant. The locking segment is translatable within the channel of the fixed segment along the longitudinal axis between locked and unlocked positions. The locking segment defines a proximal opening that passes vertically through a body of the locking segment and has locking teeth at a distal end portion thereof. The lower segment is pivotally coupled to the fixed segment about a pivot axis that is transverse to the longitudinal axis. The lower segment has a distal end portion that includes teeth that oppose the locking teeth. The upper segment is pivotally coupled to the fixed segment about the pivot axis. The upper segment has a distal end portion which includes teeth that oppose the locking teeth. The adjustable spinal implant has a collapsed configuration wherein the distal end portions of the lower and upper segments define a first height and an expanded configuration wherein the distal end portions of the lower and upper segments define a second height greater than the first height. The locking mechanism is engageable with the locking segment to translate the locking segment longitudinally between the locked and unlocked positions to fix the lower and upper segments relative to the fixed segment.

In aspects, the locking teeth of the locking segment are engaged with the teeth of the lower and upper segments to fix the lower and upper segments relative to the fixed segment to define the locked position.

In some aspects, a bottom surface of the spinal implant is defined by a lower surface of the lower segment and a lower surface of the fixed segment. In the collapsed configuration the lower surfaces of the lower segment and the fixed segment are disposed with the same linear plane and in the expanded configuration the lower surface of the lower segment and the lower surface of the fixed segment define a non-zero first angle therebetween. The first angle may be in a range of about 135° to about 179°. The top surface of the spinal implant may be defined by an upper surface of the upper segment and an upper surface of the fixed segment. In the collapsed configuration, the upper surfaces of the upper segment and the fixed surface are disposed within the same linear plane. In the expanded configuration, the upper surface of the upper segment and the upper surface of the fixed segment may define a non-zero section angle therebetween. The second angle may be in a range of about 135° to about 179°.

In certain aspects, the distal end portion of the lower segment may include tines that define a gap therebetween. Each of the tines may include the teeth that oppose the locking teeth. The distal end portion of the upper segment may include a tongue that is positionable within the gap defined between the tines of the lower segment. The tongue may include the teeth that oppose the locking teeth.

In particular aspects, the locking mechanism may include a locking screw that is disposed within the channel of the fixed segment and the passage of the locking segment. The locking mechanism may include a threaded insert that is disposed on the threaded shank of the locking screw that engages walls defining the proximal opening of the locking segment to transition the locking segment between the locked and unlocked positions.

In certain aspects, the locking teeth are arcuate in a plane parallel to the longitudinal axis. The locking teeth may have a semi-circular profile in the plane parallel to the longitudinal axis.

In another aspect of the present disclosure, a method of inserting an adjustable spinal implant includes positioning an adjustable spinal implant into an intervertebral space in a collapsed configuration, unlocking the adjustable spinal implant when the adjustable spinal implant is positioned within the intervertebral space, transitioning the adjustable spinal implant to an expanded configuration, and locking the adjustable spinal implant in the expanded configuration. The distal end portion of the adjustable spinal implant has a first height in the collapsed configuration. Unlocking the adjustable spinal implant includes disengaging locking teeth of a locking segment from teeth of a lower segment and teeth of an upper segment. Transitioning the adjustable spinal implant to the expanded configuration includes pivoting the lower segment, the upper segment, or both segments of the adjustable spinal implant about a pivot axis is defined by a fixed segment of the adjustable spinal implant such that a distal end portion of the adjustable spinal implant has a second height greater than the first height. Locking the adjustable spinal implant in the expanded configuration includes engaging the locking teeth of the locking segment with teeth of the lower segment and/or teeth of the upper segment to fix the lower segment and the upper segment relative to the fixed segment.

In aspects, unlocking the adjustable spinal implant includes rotating a locking screw disposed along a longitudinal axis of the spinal implant in a first direction to proximally translate the locking segment. Locking the adjustable spinal implant may include rotating the locking screw in a second direction opposite the first direction to distally translate the locking segment.

In some aspects, positioning the adjustable spinal implant includes approaching the intervertebral space from an anterior side of a patient's anatomy. Alternatively, positioning the adjustable spinal implant includes approaching the intervertebral space from a posterior side of a patient's anatomy. It is also contemplated that positioning the adjustable spinal implant includes approaching the intervertebral space from a lateral side of a patient's anatomy.

Further, to the extent consistent, any of the aspects described herein may be used in conjunction with any or all of the other aspects described herein.

BRIEF DESCRIPTION OF THE DRAWINGS

Various aspects of the present disclosure are described herein below with reference to the drawings, which are incorporated in and constitute a part of this specification, wherein:

FIG. 5 is a side view of the adjustable spinal implant of FIG. 1 in an unlocked and compressed configuration;

FIG. 6 is a side view of the adjustable spinal implant of FIG. 1 in a locked and compressed configuration;

FIG. 7 is a side view of the adjustable spinal implant of FIG. 1 in an unlocked and expanded configuration;

FIG. 8 is a side view of the adjustable spinal implant of FIG. 1 in a locked and expanded configuration;

FIG. 9 is a perspective view of another locking segment provided in accordance with the present disclosure;

FIG. 10 is a perspective view of another lower segment provided in accordance with the present disclosure; and FIG. 11 is a perspective view of another upper segment provided in accordance with the present disclosure.

DETAILED DESCRIPTION

Figure 1:
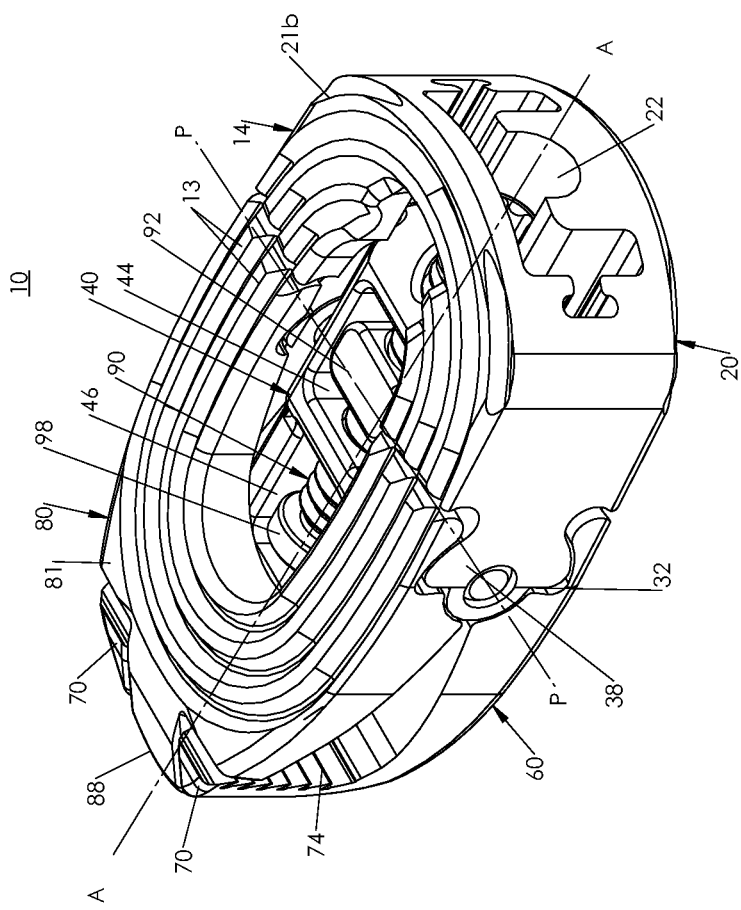
FIG. 1 is a perspective view of an exemplary adjustable spinal implant provided in accordance with the present disclosure.

Embodiments of the present disclosure are now described in detail with reference to the drawings in which like reference numerals designate identical or corresponding elements in each of the several views. As commonly known, the term "clinician" refers to a doctor, a nurse or any other care provider and may include support personnel. Additionally, the term "proximal" refers to the portion of the device or component thereof that is closer to the clinician and the term "distal" refers to the portion of the device or component thereof that is farther from the clinician. In addition, the term "cephalad" is known to indicate a direction toward a patient's head, whereas the term "caudal" indicates a direction toward the patient's feet. Further still, the term "lateral" is understood to indicate a direction toward a side of the body of the patient, i.e., away from the middle of the body of the patient. The term "posterior" indicates a direction toward the patient's back, and the term "anterior" indicates a direction toward the patient's front. Additionally, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

This disclosure relates generally to an adjustable spinal implant that is positionable within an intervertebral space in the anatomy of a patient in a compressed configuration and expandable within the intervertebral space to an expanded configuration. The adjustable spinal implant includes a lower segment and an upper segment that are each pivotally coupled to a fixed segment and a locking segment that is translatable between a locked position and an unlocked position to fix the lower and upper segments in the compressed configuration or one of a plurality of expanded configurations.

Figure 2:
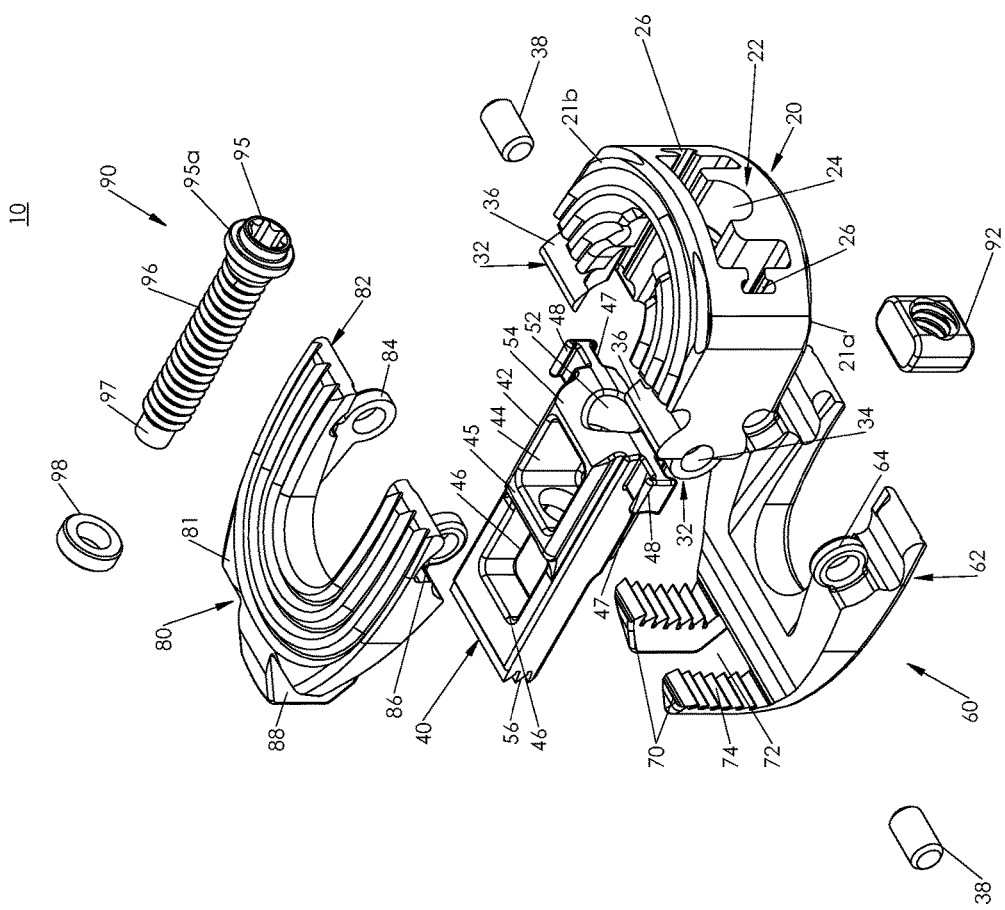
FIG. 2 is an exploded view of the adjustable spinal implant of FIG. 1, with parts separated.
Figure 4:
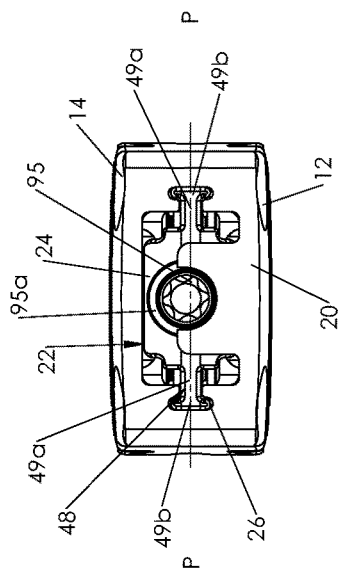
FIG. 4 is a rear view of the adjustable spinal implant of FIG. 1.
Figure 3:
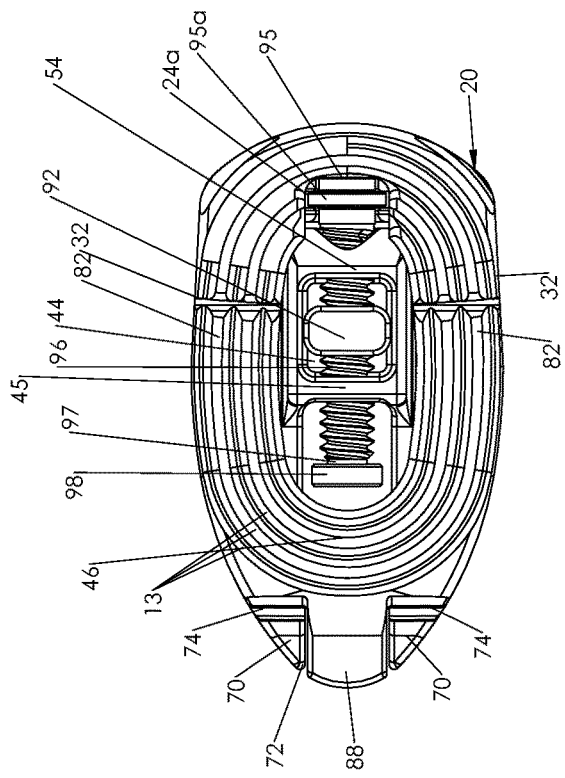
FIG. 3 is a top view of the adjustable spinal implant of FIG. 1.

Referring to FIGS. 1-5, an exemplary embodiment of an adjustable spinal implant 10 in accordance with the present disclosure includes a fixed segment 20, a locking segment 40, a lower segment 60, an upper segment 80, and a locking mechanism 90. The spinal implant 10 includes a row of teeth 11 (FIG. 5) in a stadium configuration or concentric ovals on a bottom surface 12. The bottom surface 12 is defined by a lower surface 21a of the fixed segment 20 and a lower surface 61 of the lower segment 60. The spinal implant 10 includes a row of teeth 13 in a stadium configuration on a top surface 14 of the spinal implant 10. The top surface 14 is defined by an upper surface 21b of the fixed segment 20 and an upper surface 81 of the upper segment 80.

The fixed segment 20 slidably supports the locking segment 40 and pivotally supports the lower and upper segments 60, 80. When viewed from above or below, the fixed segment 20 is substantially U-shaped with an open end of the U-shape facing distally. The fixed segment 20 defines a channel 22 that passes through the fixed segment 20 to define a longitudinal axis A-A of the spinal implant 10. The channel 22 includes a central section 24 and winged sections 26 extending laterally from the central section 24. The channel 22 is shaped to slidably receive the locking segment 40 as detailed below. The fixed segment 20 has distally extending end portions 32 on either side of the channel 22. Each end 32 defines a lateral opening 34 and reliefs 36. The lateral openings 34 define a pivot axis P-P that is orthogonal to the longitudinal axis A-A of the spinal implant 10. Each lateral opening 34 is sized to receive a pivot pin 38 which may be frictionally secured within a respective one of the lateral openings 34. The reliefs 36 are defined between the ends 32 and the lower and upper surfaces 21a, 21b of the fixed segment 20.

The locking segment 40 is translatable along the longitudinal axis A-A of the spinal implant 10 to fix the lower and upper segments 60, 80 relative to the fixed segment 20. The locking segment 40 has a body 42 which is substantially rectangular in shape when viewed from above or below. The body 42 defines a first or proximal opening 44 that passes vertically through the body 42 and a second or distal opening 46 that passes vertically through the body 42. The proximal and distal openings 44, 46 are separated by a central wall 45 of the body 42. The body 42 also defines a passage 52 that extends along the longitudinal axis A-A of the spinal implant 10 and passes through a proximal wall 54 of the body 42 and the central wall 45 of the body 42. The body 42 also includes wings 48 that laterally extend from the body 42 adjacent the proximal wall 54. Each wing 48 includes a horizontal section 49a and a vertical section 49b disposed at the end of the horizontal section 49a. The wings 48 are slidably received within the winged sections 26 of fixed segment 20 of the spinal implant 10. The distal end of the body 42 defines horizontal locking teeth 56 that are orthogonal to the longitudinal axis A-A of the spinal implant 10.

The lower segment 60 is pivotally coupled to the fixed segment 20 by proximally extending ends 62 disposed about the pivot axis P-P. Each end 62 includes a ring 64 that is positioned inside of the ends 32 of the fixed segment 20 and about the pivot axis P-P to receive one of the pivot pins 38 and includes a depression 66 (FIG. 5) that proximally extends from the respective ring 64. The depression 66 is received within a respective relief 36 of the fixed segment 20. The depression 66 supports a portion of the bottom teeth 11 (FIG. 5) that extend on the respective end 62 of the lower segment 60 such that the bottom teeth 11 transition smoothly between the respective end 62 and the respective end 32 of the fixed segment 20. The lower segment 60 also includes tines 70 that extend upwardly from a distal end portion of the lower segment 60 and define a gap 72 therebetween. The longitudinal axis A-A of the spinal implant 10 passes through the gap 72. Each of the tines 70 includes proximally facing horizontal teeth 74 that oppose the locking teeth 56 of the locking segment 40.

The upper segment 80 is pivotally coupled to the fixed segment 20 by proximally extending ends 82 disposed about the pivot axis P-P. Each end 82 includes a ring 84 that is positioned inside of the ends 32 of the fixed segment 20 and about the pivot axis P-P to receive one of the pivot pins 38. As shown, the rings 84 are positioned outside of the rings 64 of the lower segment 60; however, it is contemplated that the rings 84 may be positioned inside of the rings 64. Each end 82 also includes a depression 86 that proximally extends from the respective ring 84 and is received within a respective relief 36 of the fixed segment 20. The depression 86 supports a portion of the upper teeth 13 that extend on the respective end 82 of the upper segment 80 such that the upper teeth 13 transition smoothly between the respective end 82 and the respective end 32 of the fixed segment 20. The upper segment 80 also includes a tongue 88 that extends downward from a distal end portion of the upper segment 80. The tongue 88 is moveably disposed within the gap 72 defined between tines 70 of the lower segment 60. The tongue 88 defines proximally facing horizontal teeth 89 (FIG. 8) that oppose the locking teeth 56 of the locking segment 40.

The locking mechanism 90 translates the locking segment 40 to selectively fix the lower and upper segments 60, 80 relative to one another. The locking mechanism 90 includes a threaded insert 92, a locking screw 94, and a bushing 98. The threaded segment 92 is disposed within the proximal opening 44 of the locking segment 40. The locking screw 94 includes a head 95, a threaded shank 96 extending from the head 95, and a distal end portion 97 extending from the threaded shank 96. The bushing 98 is disposed within the distal opening 46 of the locking segment 40 and is secured about the distal end portion 97 of the locking screw 94.

With reference to FIGS. 5 and 6, the locking segment 40 has an unlocked position (FIG. 5) and a locked position (FIG. 6). In the unlocked position, the locking teeth 56 of the locking segment 40 are spaced apart from the teeth 74, 89 of the lower and upper segments 60, 80, respectively, such that the upper and lower segments 60, 80 are pivotable relative to the fixed segment 20 and one another. In the locked position, the locking teeth 56 of the locking segment 40 are engaged with the teeth 74, 89 of the lower and upper segments, 60, 80, respectively, such that the upper and lower segments 60, 80 are fixed relative to the fixed segment 20 and one another. It will be appreciated that the locking teeth 56 of the locking segment 40 are dimensioned to engage teeth 74 of each tine 70 of the lower segment 60 and teeth 89 of the tongue 88 of the upper segment simultaneously.

The locking mechanism 90 translates the locking segment 40 between the unlocked and locked positions. The head 95 of the locking screw 94 is fixed within the central section 24 of the channel 22 of the fixed segment 20. The head 95 may include a flange 95a that is received within a recess 24a defined in the central section 24 to prevent longitudinal movement of the locking screw 94 relative to the fixed segment 20. The threaded shank 96 (FIG. 3) extends along the longitudinal axis A-A of the spinal implant 10 within the channel 22 of the fixed segment 20 and through the passage 52 of the locking segment 40. As the threaded shank 96 passes through the proximal opening 44 of the locking segment 40, the threaded shank 96 passes through and threadably engages the threaded insert 92. The threaded shank 96 extends through the central wall 45 between the proximal and distal openings 44, 46 of the locking segment 40 and the bushing 98 is secured about the distal end portion 97 of the locking screw 94 to prevent the distal end portion 97 from withdrawing through the central wall 45. The bushing 98 may engage the central wall 45 to limit distal translation of the locking segment.

Referring to FIGS. 5 and 7, the spinal implant 10 has a parallel or collapsed configuration (FIG. 5) and a fully expanded configuration (FIG. 7). In the collapsed configuration, the lower segment 60 and the upper segment 80 are approximated relative to one another such that lower surface 61 of the lower segment 60 and the upper surface 81 of the upper segment 80 are substantially parallel to one another. In addition, in the collapsed configuration, the lower surface 61 of the lower segment 60 is aligned with lower surface 21a of the fixed segment 20 such that the bottom surface 12 of the spinal implant 10 is substantially planar and the upper surface 81 of the upper segment 80 is aligned with the upper surface 21b of the fixed segment 20 such that the top surface 14 of the spinal implant 10 is substantially planar. In the collapsed configuration, the tines 70 of the lower segment 60 may abut the upper segment 80 and/or the tongue 88 of the upper segment 80 may abut the lower segment 60 to limit the pivoting of the lower and upper segments 60, 80 relative to the fixed segment 20. With particular reference to FIG. 6, in the collapsed configuration the lower and upper segments 60, 80 form a beveled distal or leading end 18 (FIG. 6) of the spinal implant 10.

In one of a plurality of expanded configurations (i.e., any configuration between the fully compressed configuration and the fully expanded configuration), the lower and upper segments 60, 80 are pivoted apart from one another about the pivot axis P-P such that the lower surface 61 of the lower segment 60 and the upper surface 81 of the upper segment 80 are askew relative to one another. As shown in FIG. 7, the lower surface 61 of the lower segment 60 defines an angle $\theta_1$ with the lower surface 21a of the fixed segment 20 and the upper surface 81 of the upper segment 80 defines an angle $\theta_2$ between upper surface 21b of the fixed segment 20. In the expanded configurations at least one of the angles $\theta_1$ and $\theta_2$ is in a range between about 150° and about 175° such that a height of the spinal implant 10 between the lower surface 61 of the lower segment 60 and the upper surface 81 of the upper segment 80 adjacent the tines 70 and the tongue 88 is greater than the height of the fixed segment 20 between the lower and upper surfaces 21a, 21b thereof. It is contemplated that in the expanded configurations each of the angles $\theta_1$ and $\theta_2$ may be in a range of about 150° to about 180° (e.g., about 165°). The interaction of the depressions 66, 86 of the lower and upper segments 60, 80, respectively, and the reliefs 36 of the fixed segment 20 may form stops to limit the range of angles $\theta_1$ and $\theta_2$.

It will be appreciated that manufacturing the spinal implant 10 by standard metal machining methods (e.g., using a lathe, mill, EDM, etc.) may be difficult. Instead, it is contemplated that the spinal implant 10 are manufactured using additive manufacturing methods. One such additive manufacturing method commonly referred to as Selective Laser Powder Processing (SLPP) utilizes powdered metal and a laser which sinters or cures the metal in a selective fashion according to the design intent in thin layers, e.g., layers may have a thickness of about 250 μm. The object (e.g., spinal implant 10) is built layer by layer to allow for more design options and features which would be difficult to be machined. In addition, as spinal implant 10 is individually manufactured, it is possible to customize the spinal implant 10 for a designated patient. Suitable manufacturing methods are disclosed in U.S. Pat. No. 8,590,157, the entire contents of which are hereby incorporated by reference herein.

The spinal implant 10 may be constructed from titanium, a titanium-alloy, a cobalt-chromium alloy, a ceramic, or any other suitable biocompatible material. It is also contemplated that the spinal implant 10 may be three-dimensionally printed from a biocompatible polymer.

Referring to FIGS. 5-8, a method of inserting the adjustable spinal implant 10 into a desired intervertebral space is disclosed in accordance with the present disclosure. Initially referring to FIG. 6, the spinal implant 10 is in the collapsed configuration with the locking segment 40 in the locked position. In such a configuration, the spinal implant 10 has a minimum height to aid in insertion of the spinal implant 10 into the desired intervertebral space with each of the angles $\theta_1$ and $\theta_2$ about 180°. As shown in FIG. 6, in the collapsed configuration, the lower segment 60 and the upper segment 80 cooperate to form the beveled leading end 18 of the spinal implant 10 which may further assist in insertion of the spinal implant 10 into the desired intervertebral space. As detailed above, the locking segment 40 is in the locked position, to prevent the lower and upper segments 60, 80 from pivoting relative to the fixed segment 20. An insertion tool (not shown) may engage the channel 22 of the fixed segment 20 of the spinal implant 10 to insert the spinal implant 10 into the desired intervertebral space. It is contemplated that an anterior approach or a posterior approach may be used to insert the spinal implant 10 in accordance with the disclosed method. Alternatively, it is contemplated that a lateral approach may be used to insert the spinal implant in accordance with the disclosed method.

When the spinal implant 10 is positioned in a desired intervertebral space, a rotatable instrument (not shown) is inserted into the channel 22 to engage the head 95 of the locking screw 94. The rotatable instrument may be a screwdriver or similar instrument and may be integrally formed with the insertion tool such that the rotatable instrument is engaged with the head 95 of the locking screw 94 during insertion of the spinal implant into the desired intervertebral space. Alternatively, the rotatable instrument may be a separate instrument such that the insertion instrument is removed before the rotatable instrument engages the head 95 of the locking screw 94. Further, it is contemplated that the rotatable instrument may be inserted through the insertion instrument such that the insertion tool may remain engaged with the channel 22 of the fixed segment 20 when the rotatable instrument engages the head 95 of the locking screw 94.

With the rotatable instrument engaged with the head 95 of the locking screw, the rotatable instrument is rotated to effect rotation of the locking screw 94 in a first direction such that the threaded insert 92 is proximally translated along the threaded shank 96 of the locking screw 94. As the threaded insert 92 is proximally translated along the threaded shank 96, the threaded insert 92 engages the proximal wall 54 of the locking segment 40 that defines the proximal opening 44 of the locking segment 40 to proximally translate the locking segment 40 towards the unlocked position as shown in FIG. 5. As the locking segment 40 translates proximally, the locking teeth 56 of the locking segment 40 are disengaged from the teeth 74 of the lower segment 60 and the teeth 89 of the upper segment 80.

When the spinal implant 10 is positioned in the desired intervertebral space with the locking segment 40 in the unlocked position, at least one of the lower and upper segments 60, 80 is pivoted relative to the fixed segment 20 about the pivot axis P-P towards an expanded configuration as shown in FIG. 7. An expansion instrument may be used to pivot the lower and upper segments 60, 80 about the pivot axis P-P. As the lower and upper segments 60, 80 are pivoted about the pivot axis P-P, the spinal implant 10 is transitioned towards the expanded configuration until the leading end 18 of the spinal implant 10 has a desired height. Upon expansion each of the angles $\theta_1$ and $\theta_2$ may bin in a range of about 150° to about 180°. More preferably, in the expanded configuration each of the angles $\theta_1$ and $\theta_2$ are between about 160° and about 170°. Most preferably, in the expanded configuration each of the angles $\theta_1$ and $\theta_2$ are about 165°. When the distal end portion 18 of the spinal implant 10 reaches a desired height, the rotatable instrument inserted in the channel 22 is rotated to effect rotation of the locking screw 94 in a second direction opposite the first direction to distally translate the threaded insert distally along the threaded shank 96 of the locking screw 94. As the threaded insert 92 is translated distally along the threaded shank 96, the threaded insert 92 engages the central wall 45 of the locking segment 40 to translate the locking segment 40 distally towards the locked position until the locking teeth 56 of the locking segment 40 are engaged with the teeth 74 of the lower segment 60 and the teeth 89 of the upper segment 80 to fix the lower segment 60 and the upper segment 80 in the expanded configuration as shown in FIG. 8. As the threaded insert 92 engages the central wall 45 of the locking segment 40, the bushing 98 may engage the central wall 45 to retain the locking screw 94 within the locking segment 40. With the spinal implant 10 in the expanded configuration and the locking segment 40 in the locked position, the rotatable instrument is then withdrawn from the channel 22 to disengage from the head 95 of the locking screw 94.

Referring now to FIGS. 9-11, an alternative locking segment 140, lower segment 160, and upper segment 180 are provided in accordance with the present disclosure. The locking segment 140, the lower segment 160, and the upper segment 180 are similar to the locking segment 40, lower segment 60, and upper segment 80, respectively, with like features represented with a similar label with a "1" prefix. For reasons of brevity, only the differences with respect to the locking segment 140, the lower segment 160, and the upper segment 180 will be detailed below.

With particular reference to FIG. 9, the locking segment 140 includes arcuate horizontal locking teeth 156 in a plane substantially parallel to the longitudinal axis A-A of the spinal implant 10. As shown, the arcuate horizontal locking teeth 156 have a semi-circular profile of about 180 degrees in a plane substantially parallel to the longitudinal axis A-A, e.g., when viewed from above. It is contemplated that the arcuate horizontal locking teeth 156 may form a circular profile in a range of about 75 degrees to about 215 degrees.

With particular reference to FIG. 10, the lower segment 160 includes tines 170 that extend upwardly from a distal end portion of the lower segment 160 and define a gap 172 therebetween. Each of the tines 170 includes proximally facing arcuate horizontal teeth 174 that oppose the arcuate locking teeth 156 of the locking segment 140.

With reference to FIG. 11, the upper segment 180 includes a tongue 188 that extends downward form a distal end portion of the upper segment 180. The tongue 188 is moveably disposed within the gap 172 that is defined between the tines 170 of the lower segment 160. The tongue 188 defines proximally facing arcuate horizontal teeth 189 that oppose the locking teeth 156 of the locking segment 140.

The engagement of the arcuate locking teeth 156 and the arcuate horizontal teeth 174 of the lower segment 160 and the arcuate horizontal teeth 189 of the upper segment may provide increased engagement area as compared to the locking teeth 56 detailed above. The increased engagement area may allow the spinal implant 10 to withstand additional loading which may be seen in lower portions of the spine (e.g., the lumbar or sacrum regions).

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. An adjustable spinal implant comprising:
   a fixed segment defining a channel disposed about a longitudinal axis of the spinal implant;
   a locking segment translatable within the channel of the fixed segment along the longitudinal axis between a locked position and an unlocked position, the locking segment defining a proximal opening passing vertically therethrough, the locking segment having a distal end portion including locking teeth;
   a lower segment pivotally coupled to the fixed segment about a pivot axis that is transverse to the longitudinal axis, the lower segment having a distal end portion including teeth that oppose the locking teeth;
   an upper segment pivotally coupled to the fixed segment about the pivot axis, the upper segment having a distal end portion including teeth that oppose the locking teeth, the adjustable spinal implant having a collapsed configuration wherein the distal end portions of the lower and upper segments define a first height and an expanded configuration wherein the distal end portions of the lower and upper segments define a second height greater than the first height; and
   a locking mechanism engageable with the locking segment to translate the locking segment longitudinally between locked and unlocked positions to fix the lower and upper segments relative to the fixed segment; and
   wherein, in the unlocked position, the locking teeth are longitudinally spaced apart from the teeth of the lower and upper segments.

2. The adjustable spinal implant according to claim 1, wherein the locking teeth of the locking segment are engaged with the teeth of the lower and upper segments to fix the lower and upper segments relative to the fixed segment to define the locked position.

3. The adjustable spinal implant according to claim 1, wherein a bottom surface of the spinal implant is defined by a lower surface of the lower segment and a lower surface of the fixed segment, and wherein in the collapsed configuration the lower surfaces of the lower segment and the fixed surface are disposed within the same linear plane and in the expanded configuration the lower surface of the lower segment and the lower surface of the fixed segment define a non-zero first angle therebetween.

4. The adjustable spinal implant according to claim 3, wherein the first angle is in a range of 135° to 179°.

5. The adjustable spinal implant according to claim 1, wherein a top surface of the spinal implant is defined by an upper surface of the upper segment and an upper surface of the fixed segment, and wherein in the collapsed configuration the upper surfaces of the upper segment and the fixed surface are disposed within the same linear plane and in the expanded configuration the upper surface of the upper segment and the upper surface of the fixed segment define a non-zero second angle therebetween.

6. The adjustable spinal implant according to claim 5, wherein the second angle is in a range of 135° to 179°.

7. The adjustable spinal implant according to claim 1, wherein the distal end portion of the lower segment includes tines that define a gap therebetween, each tine including the teeth that oppose the locking teeth.

8. The adjustable implant according to claim 7, wherein the distal end portion of the upper segment includes a tongue positionable within the gap defined between the tines of the lower segment, the tongue including the teeth that oppose the locking teeth.

9. The adjustable spinal implant according to claim 1, wherein the locking mechanism includes a locking screw disposed within the channel of the fixed segment and the passage of the locking segment.

10. The adjustable implant according to claim 9, wherein the locking mechanism includes a threaded insert disposed on a threaded shank of the locking screw to engage walls defining the proximal opening of the locking segment to transition the locking segment between the locked and unlocked positions.

11. The adjustable spinal implant according to claim 1, wherein the locking teeth are arcuate in a plane parallel to the longitudinal axis.

12. The adjustable implant according to claim 11, wherein the locking teeth have a semi-circular profile in the plane parallel to the longitudinal axis.

13. A method of inserting an adjustable spinal implant, the method comprising:
positioning an adjustable spinal implant into an intervertebral space in a collapsed configuration, a distal end portion of the adjustable spinal implant having a first height in the collapsed configuration;
unlocking the adjustable spinal implant when the adjustable spinal implant is positioned within the intervertebral space by disengaging locking teeth of a locking segment from teeth of a lower segment and teeth of an upper segment such that the locking teeth are longitudinally spaced apart from the teeth of the lower and upper segments;
transitioning the adjustable spinal implant to an expanded configuration by pivoting at least one of the lower segment or the upper segment of the adjustable spinal implant about a pivot axis defined by a fixed segment of the adjustable spinal implant such that a distal end portion of the adjustable spinal implant has a second height greater than the first height; and
locking the adjustable spinal implant in the expanded configuration by engaging the locking teeth of the locking segment with the teeth of the lower segment and the teeth of the upper segment to fix the lower segment and the upper segment relative to the fixed segment.

14. The method according to claim 13, wherein unlocking the adjustable spinal implant includes rotating a locking screw disposed along a longitudinal axis of the spinal implant in a first direction to proximally translate the locking segment, and wherein locking the adjustable spinal implant includes rotating the locking screw in a second direction opposite the first direction to distally translate the locking segment.

15. The method according to claim 14, wherein positioning the adjustable spinal implant includes approaching the intervertebral space from an anterior side of a patient's anatomy.

16. The method according to claim 14, wherein positioning the adjustable spinal implant includes approaching the intervertebral space from a posterior side of a patient's anatomy.

17. The method according to claim 13, wherein positioning the adjustable spinal implant includes approaching the intervertebral space from an anterior side of a patient's anatomy.

18. The method according to claim 13, wherein positioning the adjustable spinal implant includes approaching the intervertebral space from a posterior side of a patient's anatomy.

19. The adjustable spinal implant according to claim 1, wherein any one of the locking teeth of the locking segment simultaneously engages at least one of the teeth of each of the lower and upper segments.

20. The adjustable spinal implant according to claim 1, wherein the lower and upper segments are pivotally coupled to the fixed segment by a pivot pin.

* * * * *